United States Patent [19]

Huang et al.

[11] Patent Number: 5,851,818
[45] Date of Patent: Dec. 22, 1998

[54] CONDENSED PLASMID-LIPOSOME COMPLEX FOR TRANSFECTION

[75] Inventors: Shi Kun Huang, Castro Valley; Edwin Kiyoshi Oto, Redwood City; Mohammad Hassanipour, Vallejo; Bei Jin, Union City, all of Calif.

[73] Assignee: Sequus Pharmaceuticals, Inc., Menlo Park, Calif.

[21] Appl. No.: 827,236

[22] Filed: Mar. 28, 1997

Related U.S. Application Data

[63] Continuation-in-part of Ser. No. 657,795, May 31, 1996, abandoned.

[51] Int. Cl.$^6$ .......................... C12N 15/64; A01N 25/26; B01J 13/02; C12P 21/02
[52] U.S. Cl. ...................... 435/320.1; 424/417; 424/420; 427/213.3; 435/69.1
[58] Field of Search .......................... 514/44; 435/320.1, 435/69.1; 424/417, 420; 427/231.3; 935/54

[56] References Cited

U.S. PATENT DOCUMENTS 5,614,503  3/1997  Chaudhery et al. ...................... 514/44

OTHER PUBLICATIONS

Orkin et al. Report & Recommendations of the Panel to Assess the n/h Investment in Research on Gene Therapy, 1995.
Ku et al. Biochemistry 35:5616–5623, 1996.
Wasan J. Pharm. Sci 85(4) 427–433, 1996.
Guo J. Liposome Research 3(1) 51–70, 1993.
Hofland, H.E.J., et al., "Formation of Stable Cationic Lipid/DNA Complexes for Gene Transfer," *Proc. Natl. Acad. Sci. USA* 93:7305–7309 (1996).
Gao, X., and Huang, L., "Potentiation of Cationic Liposome–Mediated Gene Delivery by Polycations,"*Biochem.* 35:1027–1036 (1996).
Li, S., and Huang, L., "Lipidic Supramolecular Assemblies for Gene Transfer,"*J. Liposome Res.* 6(3):589–608 (1996).
Liu, Y., et al., "Cationic Liposome–Mediated Intravenous Gene Delivery,"*J. Biol. Chem.* 270(42):24864–24870 (1995).
Solodin, I., et al., "A Novel Series of Amphiphilic Imidazolinium Compounds for In Vitro and In Vivo Gene Delivery," *Biochem.* 34:13537–13544 (1995).
Thierry, A.R., et al., "Systemic Gene Therapy: Biodistribution and Long–Term Expression of a Transgene in Mice, "*Proc. Natl. Acad. Sci. USA* 92:9742–9746 (1995).
Wagner, E., et al., "transferrin–Polycation–DNA Complexes: The Effect of Polycations on the Structure of the Complex and DNA Delivery to Cells,"*Proc. Natl. Acad. Sci. USA* 88:4255–4259 (1991).

*Primary Examiner*—Nancy Degen
*Attorney, Agent, or Firm*—Judy M. Mohr; Peter J. Dehlinger

[57] ABSTRACT

An improvement in a method of preparing plasmid-liposome complexes for in vivo transfection is described. The improvement includes selecting a condensing agent to condense the plasmid prior to contact with the liposomes, selecting a working medium and selecting a ratio of liposome lipid to plasmid. Also disclosed are DNA plasmid-liposome complexes formed by the method.

8 Claims, 11 Drawing Sheets

CONDENSED PLASMID-LIPOSOME COMPLEX FOR TRANSFECTION

The present invention is a continuation-in-part application of U.S. patent application for patent, Ser. No. 08/657,795, for "Plasmid-Lipid Complex For Transfection", filed May 31, 1996, now abandoned.

FIELD OF THE INVENTION

The present invention relates to an improvement in a method for preparing plasmid-liposome complexes for in vivo transfection of a gene.

References

Felgner, J., et al., *Proc. Natl. Acad. Sci. USA* 84:7413–7417 (1987).

Felgner, J., et al., *J. Tiss. Cult. Meth.* 15:63–68 (1993).

Gao, X., and Huang, L., *Biochemistry* 35:1027–1036 (1996).

Guo, L., et al., *Journal of Liposome Research* 3(1):51–70 (1993).

Li, S., and Huang, L., *Journal of Liposome Research*, 6(3):589–608 (1996).

Mulligan, R. S., *Science* 260:926–932 (1993).

Morishita, R., et al., *J. Clin. Invest.* 91:2580–2585 (1993).

Rose, J. K., U.S. Pat. No. 5,279,833 (1994).

Trubetskoy, V. S., et al., *Biochimica et Biophysica Acta* 1131:311–313 (1992).

Wagner, E., et al., *Proc. Natl. Acad. Sci. USA* 88:4255–4259 (1991).

BACKGROUND OF THE INVENTION

A variety of methods have been developed to facilitate the transfer of genetic material into specific cells, e.g., gene therapy. These methods are useful for both in vivo or ex vivo gene transfer. In the former, a gene is directly introduced (intravenously, intraperitoneally, aerosol, etc.) into a subject. In ex vivo (or in vitro) gene transfer, the gene is introduced into cells after removal of the cells from specific tissue of an individual. The transfected cells are then introduced back into the subject.

Delivery systems for achieving in vivo and ex vivo gene therapy include viral vectors, such as a retroviral vector or adenovirus vectors, microinjection, electroporation, protoplast fusion, calcium phosphate, and liposomes (Felgner, et al., 1987; Mulligan, 1993; Morishita, et al., 1993).

Liposomal mediated gene therapy has, for example, involved the use of cationic liposomes formed from LIPOFECTIN™, a reagent consisting of a cationic lipid and a neutral lipid (Felgner, et al., 1989, 1993). Other liposomal-mediated methods of gene therapy have been described (Trubetskoy, et al., 1992; Morishita, et al., 1993; Rose, 1994), where electrostatic complexes of cationic liposomes and DNA are formed. More recent approaches to liposome-based transfection compositions have included a polycation, such as protamine or polylysine, to bind the DNA to the lipid particles (Wagner, et al., 1991) or to condense the DNA (Gao and Huang, 1996; Li and Huang, 1996).

However, the liposomal-mediated gene therapy methods and compositions described to date have recognized limitations, including, for example, the toxicity of LIPOFECTIN, the large size of the DNA-liposome complexes, and rather poor in vivo transfection efficiencies.

It would be desirable, therefore, to produce a DNA plasmid-liposome complex which is relatively non-toxic, is sized for intravenous administration, and has a high transfection efficiency.

SUMMARY OF THE INVENTION

The invention includes, in one aspect, an improvement in a method of preparing a plasmid-liposome complex by condensing plasmid molecules and mixing the condensed plasmids with a suspension of cationic liposomes to form a plasmid-lipid complex for use in transfecting a host cell. The improvement includes (i) selecting as a condensing agent for condensing the plasmid molecules, a polycation selected from the group consisting of histones, poly-1-glutamine, melittin or polymyxin B, (ii) selecting as a medium for suspending the condensed plasmid molecules, a low-ionic strength aqueous medium, and (iii) selecting a ratio of liposome lipid to plasmid of greater than 10 nmole liposome lipid/µg plasmid and less than 15 nmole liposome lipid/µg plasmid. The plasmid-liposome complexes produced by the improvement are characterized by (i) substantially homogeneous sizes in the range of 120–180 nm and (ii) a transfection stability of at least 30 days, as evidenced by a stable in vivo transfection efficiency of the complex after storage for 30 days at 4° C.

In one embodiment of the method, the condensing agent is selected from the group consisting of total histone, histone 1 and histone 4. In a preferred embodiment, the condensing agent is total histone.

In another embodiment, the liposome lipid to plasmid ratio is between 12–14 nmole liposome lipid/µg plasmid.

The low-ionic strength aqueous medium is prepared, in another embodiment, from a non-ionic osmotic solute, such as, glucose, sucrose or dextran.

The cationic liposomes for use in the complex can be prepared from cholesterol and the vesicle-forming lipid dimethyldioctadecylammonium (DDAB). In one embodiment, the cationic liposomes have a surface coating of polyethylene glycol by including a vesicle-forming lipid derivatized with polyethylene glycol.

The plasmid-liposome complex prepared according to the method of the invention, in one embodiment, is for use in transfecting a host cell with a gene contained in a DNA plasmid, where the DNA plasmid contains a gene selected from the group consisting of genes encoding for Factor VIII, interleukin-2 or p53.

In a preferred embodiment, the plasmid-liposome complex is for use in transfecting a host cell in the lung of a subject with a DNA plasmid containing cystic fibrosis transmembrane conductance regulator or, for lung carcinomas, cytokines, such as interleukin-2, or tumor suppressor genes, such as p53.

These and other objects and features of the invention will become more fully apparent when the following detailed description of the invention is read in conjunction with the accompanying drawings.

DETAILED DESCRIPTION OF THE INVENTION

I. Plasmid-Liposome Complex

Figure 1:
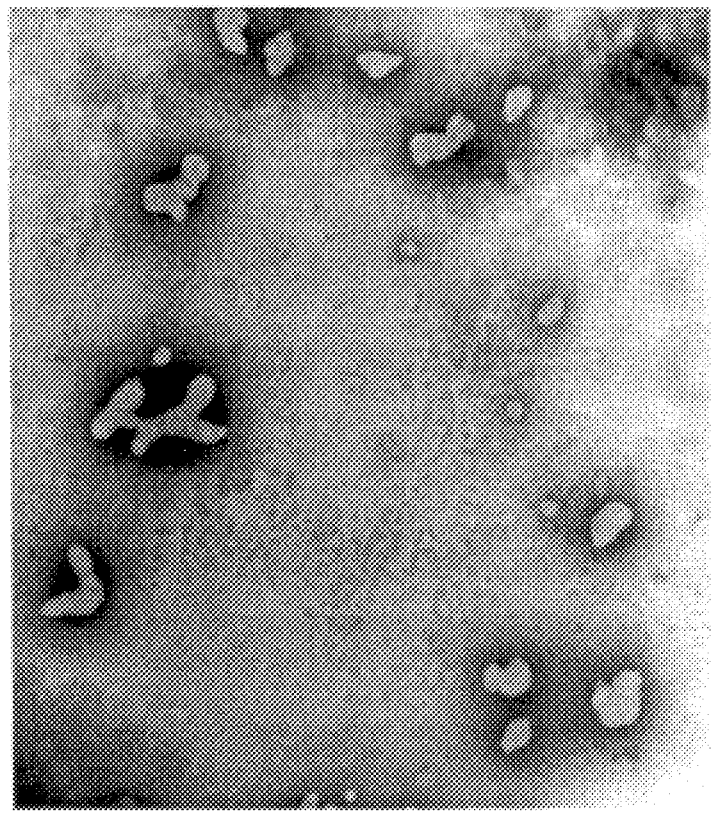
FIG. 1 is a computer-generated image of an electron micrograph of a plasmid condensed with the polycationic polymer total histone.

The present invention is directed to an improvement in a method of preparing a plasmid-liposome complex for use in vivo transfection of a host cell. The method generally includes condensing plasmid molecules by suspending the plasmids in a medium containing a condensing agent. The condensed plasmid molecules are mixed with lipid particles, such as liposomes, to form plasmid-liposome complexes. The improvement in the general method, as will be described, relates to selection of the condensing agent, selection of the suspension medium and selection of the liposome lipid to plasmid ratio. Before describing the improved preparation procedure in detail, the plasmid-liposome complex and its components will be described.

A. Cationic Liposome Components and Preparation

As described above, the plasmid-liposome complex includes condensed plasmid molecules and liposomes. Liposomes, as used herein, refer to lipid vesicles having an outer lipid shell, typically formed on one or more lipid bilayers, encapsulating an aqueous interior.

In a preferred embodiment, the liposomes are cationic liposomes composed of between about 20–80 mole percent of a cationic vesicle-forming lipid, with the remainder of neutral vesicle-forming lipids. As defined herein, "vesicle-forming lipid" is intended to include any amphipathic lipid having hydrophobic and polar head group moieties, and which (a) by itself can form spontaneously into bilayer vesicles in water, as exemplified by phospholipids, or (b) is stably incorporated into lipid bilayers in combination with phospholipids, with its hydrophobic moiety in contact with the interior, hydrophobic region of the bilayer membrane, and its polar head group moiety oriented toward the exterior, polar surface of the membrane. A major type of vesicle-forming lipid is a diacyl-chain lipid, such as a phospholipid, whose acyl chains are typically between about 14–22 carbon atoms in length, and have varying degrees of unsaturation. Another example is cholesterol and cholesterol derivatives, such as cholesterol.

A cationic vesicle-forming lipid is one whose polar head group with a net positive charge, at the operational pH, e.g., pH 4–9. Typical example include phospholipids, such as phosphatidylethanolamine, whose polar head groups are derivatized with a positive moiety, e.g., lysine, as illustrated, for example, for the lipid DOPE derivatized with L-lysine (LYS-DOPE) (Guo, et al., 1993). Also included in this class are the glycolipids, such as cerebrosides and gangliosides having a cationic polar head-group.

Another cationic vesicle-forming lipid which may be employed is cholesterol amine and related cationic sterols. Exemplary cationic lipids include 1,2-diolelyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxyethylammonium bromide (DORIE); N-[1-(2,3-dioleyloxy)propyl]-N,N,N-trimethylammonium chloride (DOTMA); 3β[N-(N',N'-dimethylaminoethane) carbamoyl] cholesterol (DC-Chol); and dimethyldioctadecylammonium (DDAB).

The remainder of the liposomes are formed of neutral vesicle-forming lipids, meaning vesicle forming lipids which have no net charge or which may include a small percentage of lipids having a negative charge in the polar head group. Included in this class of lipids are the phospholipids, such as phosphatidylcholine (PC), phosphatidyl ethanolamine (PE), phosphatidylinositol (PI), and sphingomyelin (SM), and cholesterol and other uncharged sterols.

The above-described lipids can be obtained commercially, or prepared according to published methods. Other lipids that can be included in the invention are glycolipids, such as cerebrosides and gangliosides.

The liposomes may be provide with a surface coating of hydrophilic polymer chains, effective to extend the blood circulation time of the plasmid/liposome complexes. Suitable hydrophilic polymers include polyethylene glycol (PEG), polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethyl-cellulose. A preferred hydrophilic polymer chain is polyethyleneglycol (PEG), preferably as a PEG chain having a molecular weight between 500–10,000 daltons, more preferably between 1,000–5,000 daltons. The hydrophilic polymer may have solubility in water and in a non-aqueous solvent, such as chloroform.

The coating is preferably prepared by including in the vesicle-forming lipids forming the liposomes, between 1–20 mole percent of a vesicle-forming lipid, preferably a phospholipid or other diacyl-chain lipid, derivatized at its head group with the polymer chain. Exemplary methods of preparing such lipids, and forming polymer coated liposomes therewith, have been described in co-owned U.S. Pat. Nos. 5,013,556, and 5,395,619, which are incorporated herein by reference. The polymer may be stably coupled to the lipid, or coupled through an unstable linkage which allows the coated particles to shed their coating as they circulate in the bloodstream.

The plasmid-liposome complexes may also contain an affinity moiety effective to bind specifically to target cells at which the therapy is aimed. Such moieties can be attached to the surface of the liposome or to the distal ends of hydrophilic polymer chains. Exemplary moieties include antibodies, ligands for specific binding to target cell surface receptors and the like, as described, for example, in co-owned PCT application No. WO US94/03103. The moiety can also be a hydrophobic segment to facilitate fusion of the complex with a target cell.

B. Condensed Plasmid

This section describes the preparation of the condensed-phase plasmid employed in the plasmid-liposome complex of the invention.

Polycationic condensing agents used to condense the plasmid are multiply charged cationic polymers, typically biopolymers such as such as spermidine, spermine, polylysine, protamine, total histone, specific histone fractions such as H1, H2, H3, H4, and other polycationic polypeptides, but may also include biocompatible polymers, such as polymyxin B. In a preferred embodiment, the polycationic condensing agent is a histone, which, as referred to herein, includes total histone or specific histone fractions.

Plasmids suitable for use in the complex are preferably circularized or closed double-stranded molecules having sizes preferably in the 5–40 Kbp (kilo basepair) range. The plasmids are constructed according to well-known methods and include a therapeutic gene, i.e., the gene to be expressed in gene therapy, under the control of suitable promoter and terminator control elements, and other elements necessary for replication within the host cell and/or integration into the host-cell genome. Methods for preparing plasmids useful for gene therapy in genes or other mammals are widely known and referenced.

The genes to be introduced for gene therapy by the complex of the invention generally fall into one of three categories:

In the first are those genes which are intended to overcome a gene deficiency or defect in the subject, i.e., where the subject fails to produce active, endogenous protein at all or within normal levels, and the gene introduced in the plasmid is intended to make up this deficiency. Examples of this class of genes include genes encoding adenosine deaminase (ADA), for gene expression in stem cells or lymphocytes; genes encoding purine nucleoside phosphorylase deficiency, deficiency in prostaglandin G/H synthase, therapy of Lesch-Nyhan syndrome caused by a deficiency in hypoxanthine-guanine phosphoribosyltransferase, genes encoding a variety of circulating proteins, such as $\alpha_1$-antitrypsin, clotting factors (e.g., Factor VIII, Factor IX) and globins (e.g., $\beta$-globin, hemoglobin), for the treatment of hemophilia, sickle-cell anemia and other blood-related diseases, and genes encoding hormones and other peptide regulators.

In the second class are polypeptides designed to treat any existing pathology, such as cancer, or a pathogenic condition such as viral infection. Examples include gene therapy to supply the p53 gene for cancer therapy, the gene for the CD4 peptide to inhibit HIV infection, the gene for the Pseudomonas peptide to inhibit binding of Pseudomonas to epithelial cells, and specific antibody genes to inhibit a targeted pathogen.

The third class includes genes intended to produce an mRNA transcript that can act as an antisense molecule to inhibit an undesirable protein expression, such as overexpression of proteins specific for tumor growth, or expression of viral proteins.

II. Preparation and Characterization of the Complex

In accordance with the invention, it has been discovered that a plasmid-liposome complex formed by mixing condensed-phase plasmid and cationic liposomes, in a low ionic strength medium, produces liposomes characterized by: substantially homogeneous sizes in the range 120–180 nm, and a transfection stability of at least 30 days, as evidenced by a stable in vivo transfection efficiency of the complex after storage for 30 days at 4° C.

The condensed-phase plasmid is formed by adding to the plasmid, in a low-ionic strength medium, a polycationic polymer condensing agent of the type identified above. The cationic polymer is added to the plasmid solution to a preferred concentration at which charge stoichiometry is achieved, i.e., where the total number of charges in the cationic polymer (as determined from the polymer's known charge density/weight) is at least as great as the total negative charge of the DNA (as determined from the weight amount plasmid and the known charge density of DNA/weight). Typically, the weight ratio of added DNA plasmid to added polymer is between about 0.1–5.0, more preferably, between 0.3–2.0. The condensing agent is preferably added slowly to the plasmid suspension with stirring, e.g., over a 10 minute period.

The condensed plasmid and cationic liposomes, both contained in a low-ionic strength medium, are then mixed, e.g., by slow addition of the condensed plasmid to the liposomes. The ratio of liposome lipids to plasmid is an important parameter for achieving maximum transfection. That ratio, in nmole liposome lipid/$\mu$g plasmid, is preferably greater than 10 but less than 15, most preferably between 12–14.

As indicated above, a critical feature of the invention is the mixing of liposomes and condensed phase plasmid in a low ionic-strength medium. Preferably the final concentration of the medium, including ions present in the DNA, condensing agent, and liposome lipid species, is less than the ionic strength of a 25 mM monovalent ionizable salt, such as NaCl, and preferably less than 10 mM of such salt, more preferably less than about 1 mM. In general, low ionic strength is readily obtained by employing free base or free acid plasmid, polycation, and lipid species, (ii) removing electrolyte components, or alternatively, employing sufficiently dilute concentrations of the components to maintain a low ionic strength, and/or removing electrolytes generated from the components by dialysis or the like. At the same time, it is useful to prepare the composition in the presence of a non-electrolyte solute such as glucose to provide an osmotic balance as an injectable formulation.

FIG. 1 is a computer-generated image of a negative-stain transmission electron micrograph of a luciferase-encoding PNSL plasmid condensed with total histone, as described in Example 1. As seen, the plasmid is condensed into discrete, single particles of about 100 nm in diameter and less.

Figure 2:
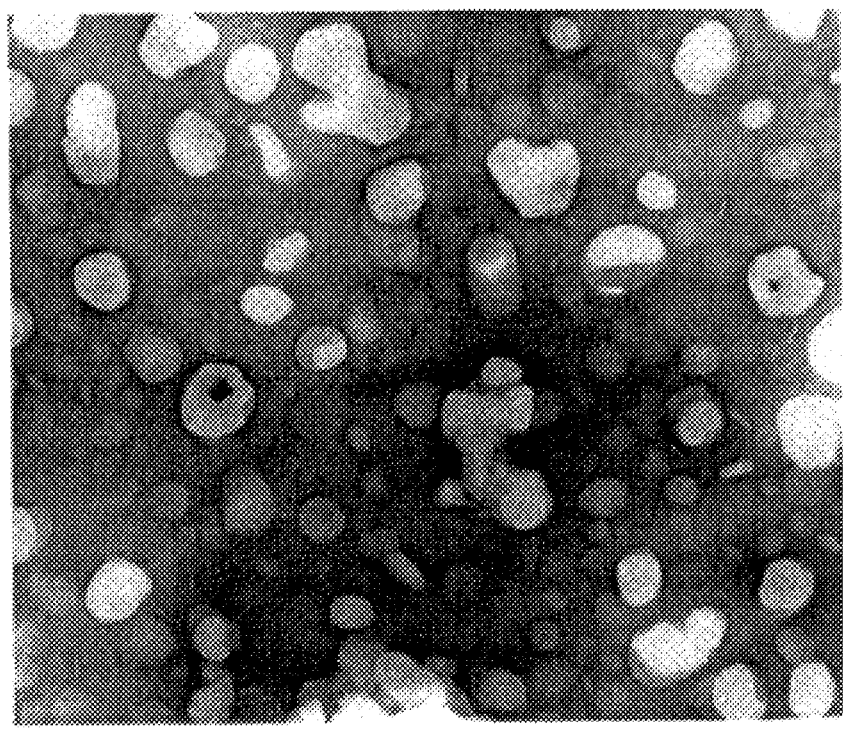
FIG. 2 is a computer-generated image of an electron micrograph of a polycation-condensed plasmid complexed with cationic liposomes in accordance with the invention.

FIG. 2 is a computer-generated image of a negative-stain transmission electron micrograph of a polycation-condensed plasmid-liposome complex prepared as described in Example 1. In comparing the neat, condensed plasmid molecules in FIG. 1 with the complex of FIG. 2, the opaque, condensed plasmids are readily apparent in FIG. 2. Also visible in FIG. 2 is a transparent membrane which surrounds each condensed plasmid. This transparent membrane is the liposome lipid bilayer which coats each condensed plasmid.

Figure 3A:
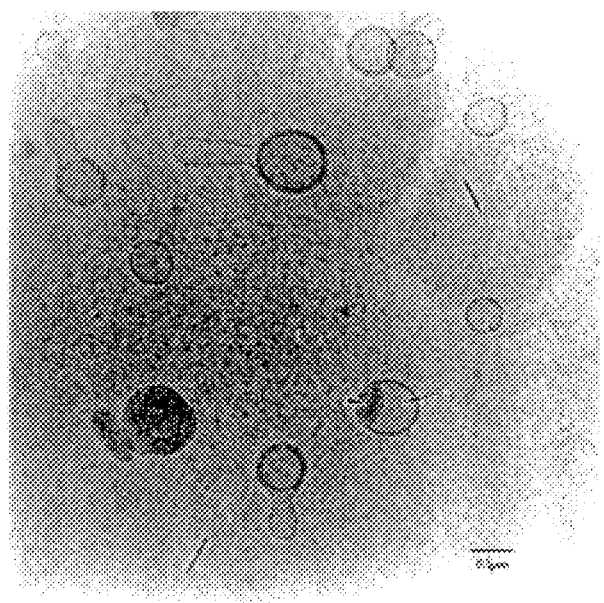
FIGS. 3A–3B are computer-generated images of cryogenic (FIG. 3A) and freeze fracture (FIG. 3B) transmission electron micrographs of a polycation-condensed plasmid complexed with cationic liposomes in accordance with the invention.
Figure 3B:

FIGS. 3A–3B are computer-generated images of cryo-electron and freeze fracture transmission electron micrographs of the plasmid-liposome complex prepared as described in Example 1. The micrograph in FIG. 3A is obtained by freezing a thin layer of plasmid-liposome complex suspension and viewing the layer under a cryoelectro microscope. The micrograph shows single, discrete plasmid-liposome complexes, where the condensed DNA is visible as a darker central region in many of the particles. The freeze-fracture micrograph of FIG. 3B also shows discrete plasmid-liposome complexes, with no apparent aggregation.

Figure 4:
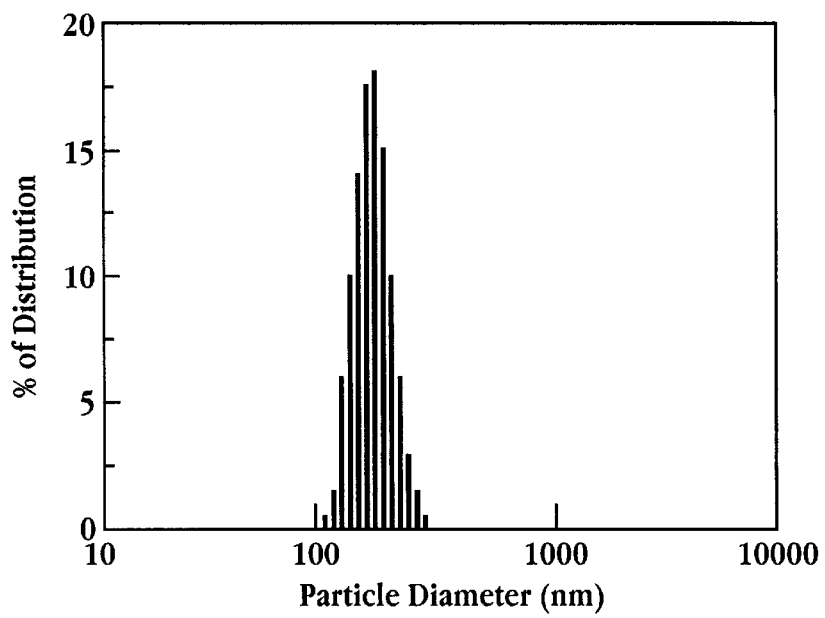
FIG. 4 is a plot showing the size, in nm as measured by dynamic light scattering, of plasmid-liposome complexes prepared in accordance with the invention.

Dynamic light scattering was used to determine the average complex size and size distribution. The results are shown in FIG. 4 which shows that the complexes as prepared in Example 1 form a homogeneous population having an average size of about 146 nm (standard deviation of 45 nm).

Figure 5:
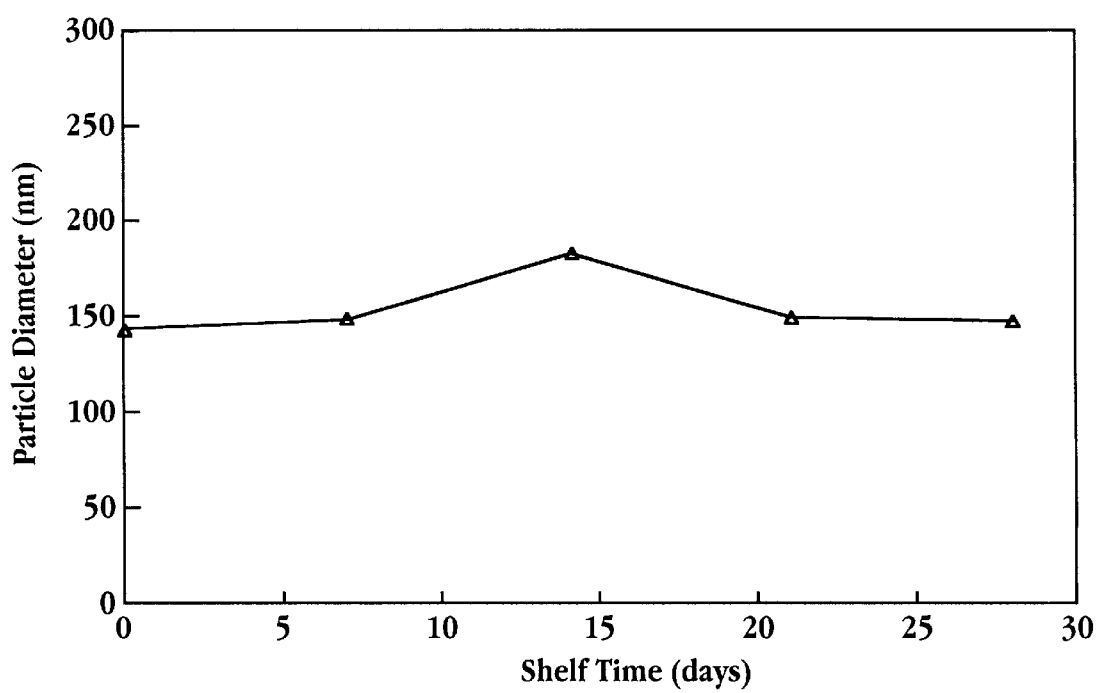
FIG. 5 is a plot of particle diameter, in nm as measured by dynamic light scattering, as a function of storage time at 4° C., for plasmid-liposome complexes of the invention.

According to an important feature of the invention, the plasmid-liposome complexes are stable, that is, the complexes maintain their initial size, e.g., there is little aggregation of the complexes, and retain therapeutic activity, for at least 30 days. FIG. 5 provides evidence of complex size stability and shows the complex size, as measured by dynamic light scattering, as a function of time. A suspension of the plasmid-liposome complexes in water/glucose were stored at 4° C. and analyzed at one week intervals. Initially after complex formation, the average complex size was about 150 nm. After 4 weeks of storage, the complex size remained at about 150 nm. Complex stability with respect to retention of therapeutic activity is discussed below in FIG. 11.

III. In vivo Transfection

Plasmid-liposome complexes prepared in accordance with the invention were administered to mice to determine the transfection efficiency of various plasmid-liposome complex formulations and to determine stability of transfection, biodistribution of the complex, pharmacokinetics and dose response. The in vivo transfection procedure is described in Example 2.

Figure 6:
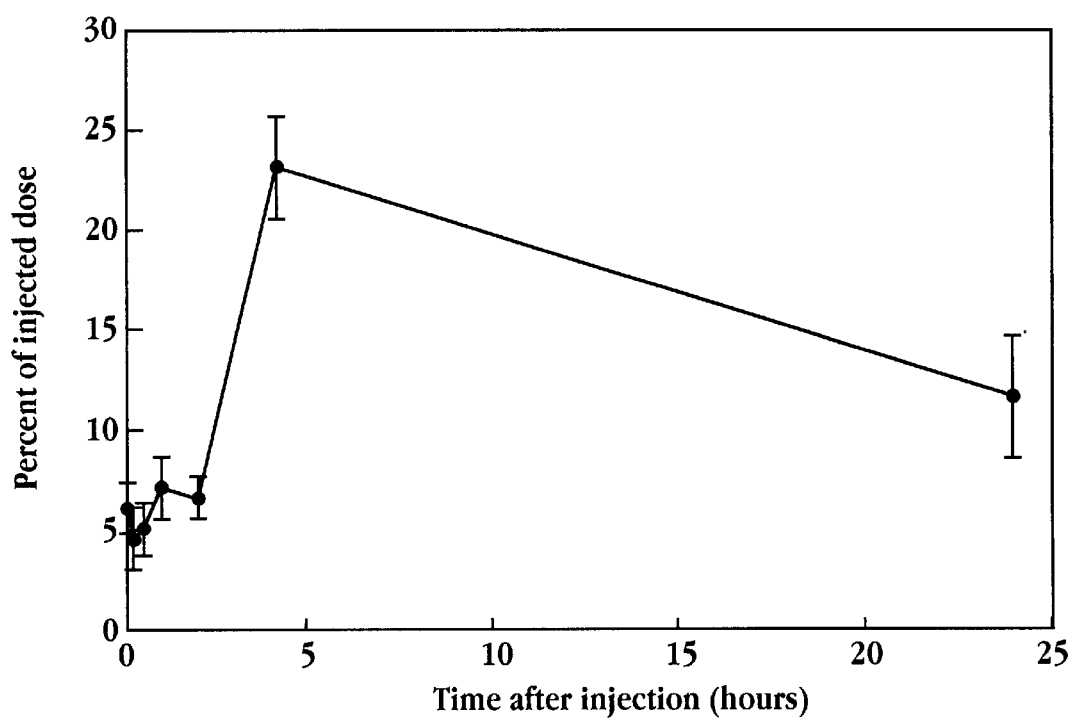
FIG. 6 is a plot of percent of injected dose as a function of time after intravenous injection in mice of labelled plasmid-liposome complexes of the invention.

The pharmacokinetics of plasmid-liposome complexes were determined by injecting complexes including an $S^{35}$-labelled DNA plasmid into mice. FIG. 6 shows the percent of injected dose as a function of time after intravenous injection. Immediately after injection of the plasmid-liposome complex dose, about 7% of the injected dose is in the blood stream. Other studies indicate that immediately after injection, the complexes localize in the lung. After a period of time the complexes are neutralized by serum proteins in the lung and enter the blood stream, evidenced by the increase in the percentage of injected dose at the 5 hour time point (FIG. 6). The complexes are then cleared from the bloodstream, with about 12% of the injected dose present at 24 hours.

Plasmid-liposome complexes were prepared for in vivo administration with varying ratios of liposome lipid to plasmid. The complexes were prepared according to the general procedure set forth in Example 1 by varying the amount of polycation condensing agent, and the total amount of liposome lipids. Typically, the amount of polycation condensing agent varied between 100–500 μg and the liposome lipid/plasmid ratio varied between 8–18 nmoles lipid/μg plasmid.

FIGS. 7–9 shows the results for plasmid-liposome complexes prepared with total histone (FIGS. 7A–7E), histone H1 (FIGS. 8A–8E) and histone H4 (FIGS. 9A–9E) as the polycationic condensing agents. After administration of the complex, prepared from the formulations indicated in the Tables below, luciferase expression was measured in the lung, liver, heart, spleen and kidney.

Table 1 summarizes the compositions for the plasmid-liposome complexes prepared using total histone as the polycationic condensing agent. The amount of total histone was varied between 100–500 μg to vary the ratio of plasmid/total histone from 0.2–1.0. The ratio of liposome lipids/plasmid was also varied and ratios of 8, 14 and 18 nmoles liposome lipids/μg plasmid were tested.

TABLE 1

| | Formulation Number[1] | | | | | |
|---|---|---|---|---|---|---|
| Component | 1 | 2 | 3 | 4 | 5 | 6 |
| pNSL plasmid, μg | 100 | 100 | 100 | 100 | 100 | 100 |
| total histone, μg | 200 | 100 | 200 | 350 | 500 | 200 |
| μmoles liposome lipids[2] | 0.8 | 1.4 | 1.4 | 1.4 | 1.4 | 1.8 |
| μg plasmid/μg total histone | 0.5 | 1.0 | 0.5 | 0.3 | 0.2 | 0.5 |
| nmoles lipids/μg plasmid | 8 | 14 | 14 | 14 | 14 | 18 |

[1]Formulation number corresponds to FIGS. 7A–7E.
[2]Liposome prepared from 1:1 mole ratio of DDAB:cholesterol.

Figure 7A:
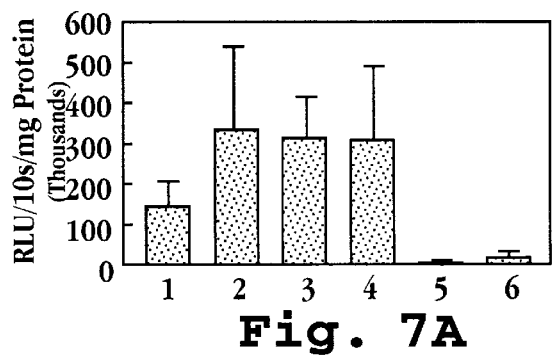
FIGS. 7A–7E show luciferase expression, in relative light units (RLU)/10 seconds/mg protein, in the lung (FIG. 7A), liver (FIG. 7B), heart (FIG. 7C), spleen (FIG. 7D) and kidney (FIG. 7E) for plasmid-liposome complexes prepared with total histone.
Figure 7B:
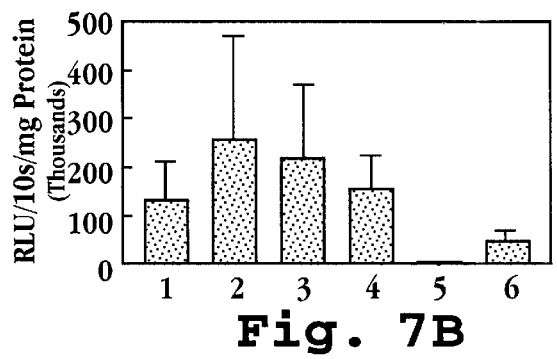
Figure 7C:
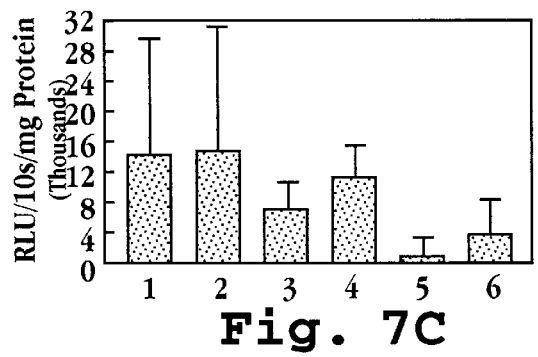
Figure 7D:
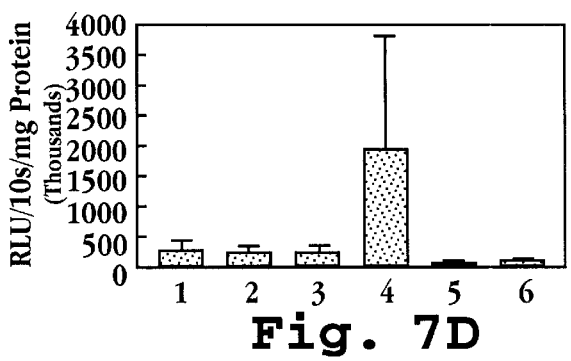
Figure 7E:
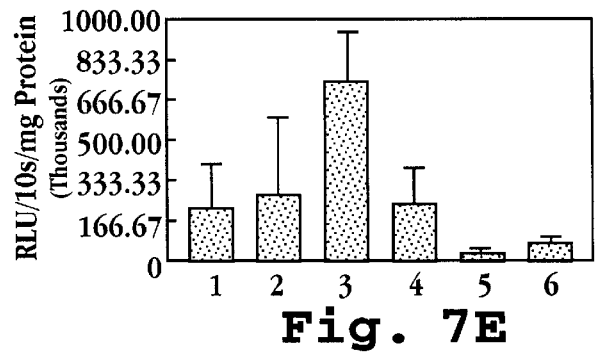

The results of in vivo administration in mice of the formulations summarized in Table 1 are shown in FIGS. 7A–7E, where luciferase expression, in relative light units (RLU)/10 seconds/mg protein, is shown in the lung (FIG. 7A), liver (FIG. 7B), heart (FIG. 7C), spleen (FIG. 7D) and kidney (FIG. 7E). The figures indicate that there is a window where the transfection is highest. Specifically, for total histone as the condensing agent, the transfection is highest where the liposome lipid/plasmid ratio is greater than 8 nmoles lipid/μg plasmid and less than 18 nmoles lipid/μg.

Table 2 summarizes the plasmid-liposome complex compositions prepared and tested in vivo using histone H1 as the polycationic condensing agent. The ratio of plasmid/histone Hi ratio was 0.3 or 0.5 and the liposome lipid/plasmid ratio was varied from 8, 14 and 18 nmoles lipid/μg plasmid.

TABLE 2

| | Formulation Number[1] | | | | |
|---|---|---|---|---|---|
| Component | 7 | 8 | 9 | 10 | 11 |
| pNSL plasmid, μg | 100 | 100 | 100 | 100 | 100 |
| histone H1, μg | 350 | 200 | 350 | 200 | 350 |
| μmoles liposome lipids[2] | 0.8 | 1.4 | 1.4 | 1.4 | 1.4 |
| μg plasmid/μg histone H1 | 0.3 | 0.5 | 0.3 | 0.5 | 0.3 |
| nmoles lipids/μg plasmid | 8 | 14 | 14 | 18 | 18 |

[1]Formulation number corresponds to FIG. 8A–8E.
[2]Liposome prepared from 1:1 mole ratio of DDAB:cholesterol.

The results of in vivo administration in mice of the formulations summarized in Table 2 are shown in FIGS. 8A–8E, where luciferase expression, in relative light units (RLU)/10 seconds/mg protein, is shown in the lung (FIG.

Figure 8A:
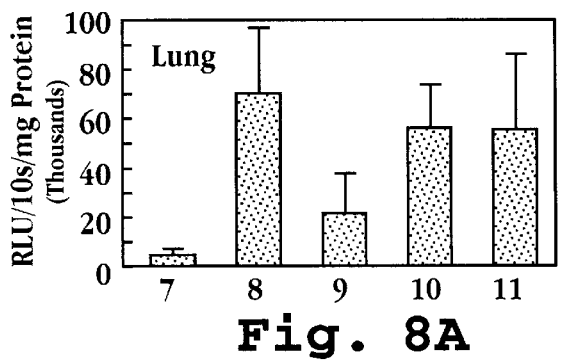
FIGS. 8A–8E show luciferase expression, in relative light units (RLU)/10 seconds/mg protein, in the lung (FIG. 8A), liver (FIG. 8B), heart (FIG. 8C), spleen (FIG. 8D) and kidney (FIG. 8E) for plasmid-liposome complexes prepared with histone H1.
Figure 8B:
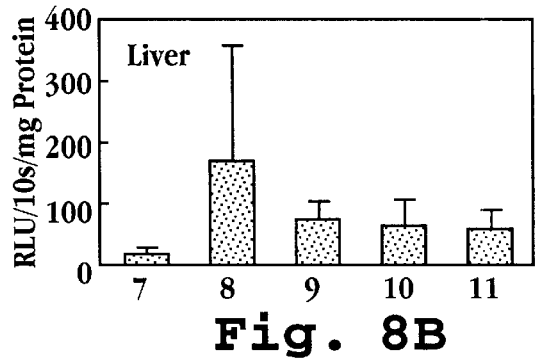
Figure 8C:
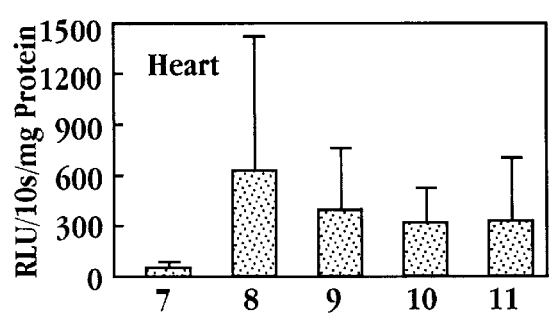
Figure 8D:
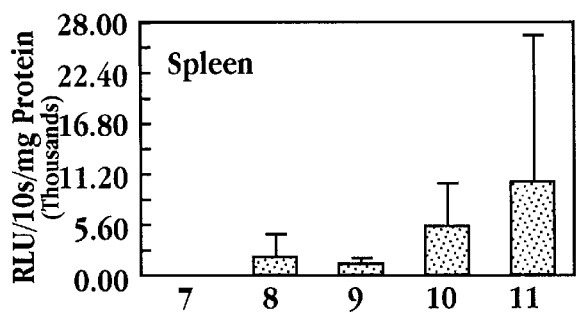
Figure 8E:
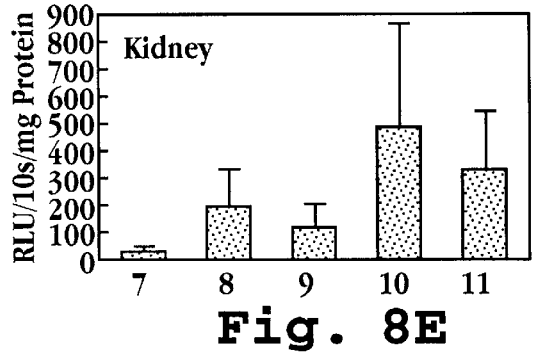

8A), liver (FIG. 8B), heart (FIG. 8C), spleen (FIG. 8D) and kidney (FIG. 8E). The figures indicate that the best transfection is achieved at a liposome lipid/plasmid ratios of 14 and 18.

Tables 3A and 3B summarize the formulations of plasmid-liposome complexes formed using histone H4 as the polycationic condensing agent. The plasmid/histone H4 ratio varied from 0.2, 0.3 or 0.5 and the liposome lipid/plasmid ratio was varied from 8, 14 or 18 nmoles lipid/$\mu$g plasmid.

TABLE 3a

|  | Formulation Number[1] | | | |
|---|---|---|---|---|
| Component | 12 | 13 | 14 | 15 |
| pNSL plasmid, $\mu$g | 100 | 100 | 100 | 100 |
| histone H4, $\mu$g | 200 | 350 | 500 | 200 |
| $\mu$moles liposome lipids[2] | 0.8 | 0.8 | 0.8 | 1.4 |

TABLE 3a-continued

|  | Formulation Number[1] | | | |
|---|---|---|---|---|
| Component | 12 | 13 | 14 | 15 |
| $\mu$g plasmid/$\mu$g histone H4 | 0.2 | 0.3 | 0.2 | 0.5 |
| nmoles lipids/$\mu$g plasmid | 8 | 8 | 8 | 14 |

[1]Formulation number corresponds to FIG. 9A–9E.
[2]Liposome prepared from 1:1 mole ratio of DDAB:cholesterol.

TABLE 3b

|  | Formulation Number[1] | | | | |
|---|---|---|---|---|---|
| Component | 16 | 17 | 18 | 19 | 20 |
| pNSL plasmid, $\mu$g | 100 | 100 | 100 | 100 | 100 |
| histone H4, $\mu$g | 350 | 500 | 200 | 350 | 500 |
| $\mu$moles liposome lipids[2] | 1.4 | 1.4 | 1.8 | 1.8 | 1.8 |
| $\mu$g plasmid/$\mu$g histone H4 | 0.3 | 0.2 | 0.5 | 0.3 | 0.2 |
| nmoles lipids/$\mu$g plasmid | 14 | 14 | 18 | 18 | 18 |

[1]Formulation number corresponds to FIG. 9A–9E.
[2]Liposome prepared from 1:1 mole ratio of DDAB:cholesterol.

Figure 9A:
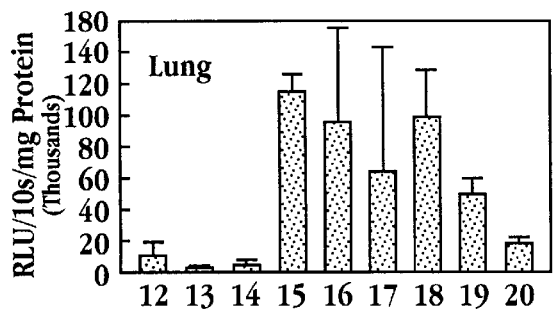
FIGS. 9A–9E show luciferase expression, in relative light units (RLU)/10 seconds/mg protein, in the lung (FIG. 9A), liver (FIG. 9B), heart (FIG. 9C), spleen (FIG. 9D) and kidney (FIG. 9E) for plasmid-liposome complexes prepared with histone H4.
Figure 9B:
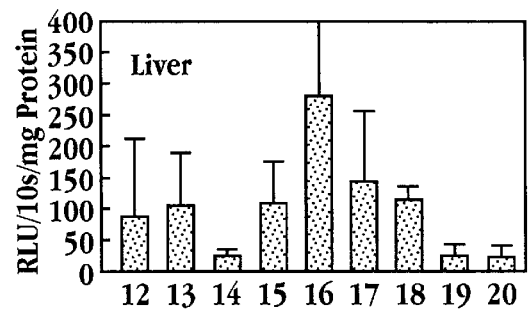
Figure 9C:
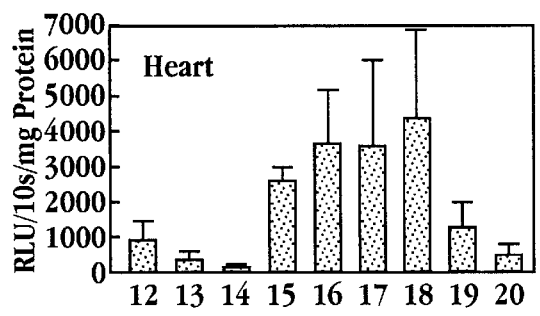
Figure 9D:
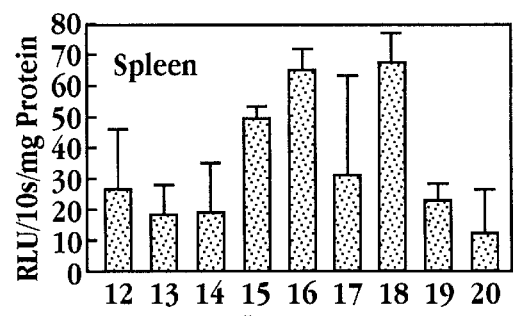
Figure 9E:
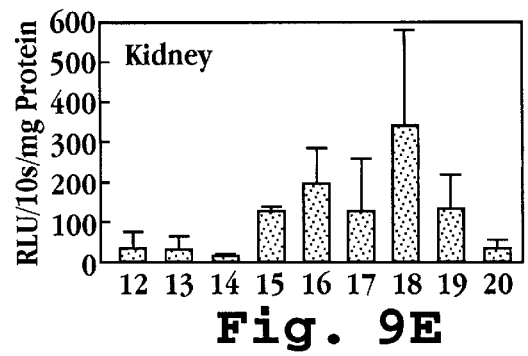

The results of in vivo administration in mice of the formulations summarized in Tables 3A and 3B are shown in FIGS. 9A–9E, where luciferase expression, in relative light units (RLU)/10 seconds/mg protein, is shown in the lung (FIG. 9A), liver (FIG. 9B), heart (FIG. 9C), spleen (FIG. 9D) and kidney (FIG. 9E). There is a window where transfection is highest of greater than 8 nmoles liposome lipid/$\mu$g plasmid and less than 18 nmoles liposome lipid/$\mu$g plasmid.

In other experiments performed in support of the present invention, plasmid-liposome complexes were prepared using poly-1-glutamine, melittin (a low molecular weight peptide containing 26 amino acids) or polymyxin B sulfate as polycationic condensing agents. Each of these are commercially available from Sigma Chemical Co. The complexes were injected in mice, as described Example 2, and in vivo transfection was measured by determining luciferase expression.

Table 4 summarizes the plasmid-liposome complex compositions prepared using poly-1-glutamine, melittin or polymyxin B as polycationic condensing agents. The amount of condensing agent was varied from 50–200 $\mu$g.

TABLE 4

| | Formulation Number[1] | | | | | | | | |
|---|---|---|---|---|---|---|---|---|---|
| condensing agent | Poly-1-glutamine | | | melittin | | | polymyxin B | | |
| Formulation No. | 21 | 22 | 23 | 24 | 25 | 26 | 27 | 28 | 29 |
| pNSL plasmid, $\mu$g | 100 | 100 | 100 | 100 | 100 | 100 | 100 | 100 | 100 |
| $\mu$g condensing agent | 50 | 100 | 200 | 50 | 100 | 200 | 50 | 100 | 200 |
| $\mu$moles liposome lipids[2] | 1.4 | 1.4 | 1.4 | 1.4 | 1.4 | 1.4 | 1.4 | 1.4 | 1.4 |
| $\mu$g plasmid/$\mu$g condensing agent | 2 | 1 | 0.5 | 2 | 1 | 0.5 | 2 | 1 | 0.5 |
| nmoles lipids/$\mu$g plasmid | 14 | 14 | 14 | 14 | 14 | 14 | 14 | 14 | 14 |

[1]Formulation number corresponds to data in FIGS. 10A–10E.
[2]Liposome prepared from 1:1 mole ratio of DDAB:cholesterol.

Figure 10A:
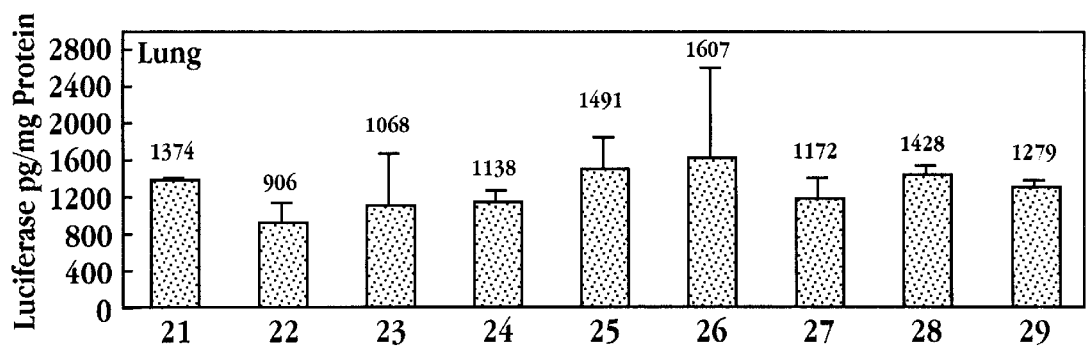
FIGS. 10A–10E show luciferase expression, in pg luciferase/mg protein, in the lung (FIG. 10A), liver (FIG. 10B), heart (FIG. 10C), spleen (FIG. 10D) and kidney (FIG. 10E) for plasmid-liposome complexes prepared with poly-1-glutamine, melittin or polymyxin B as the cationic condensing agent.
Figure 10B:
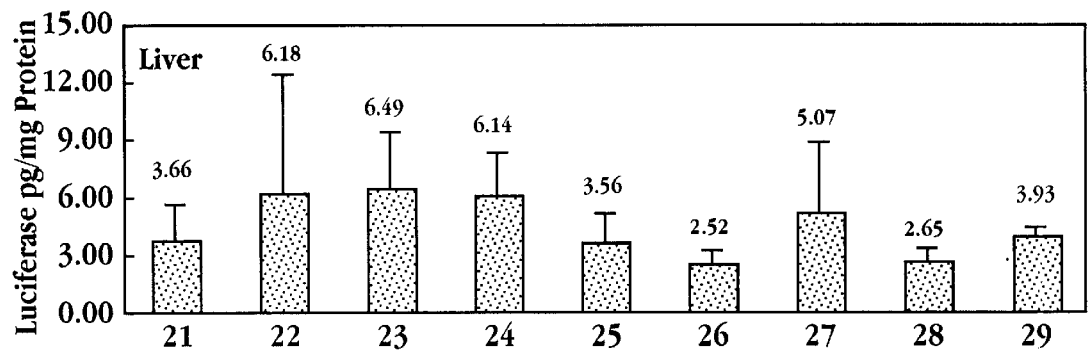
Figure 10C:
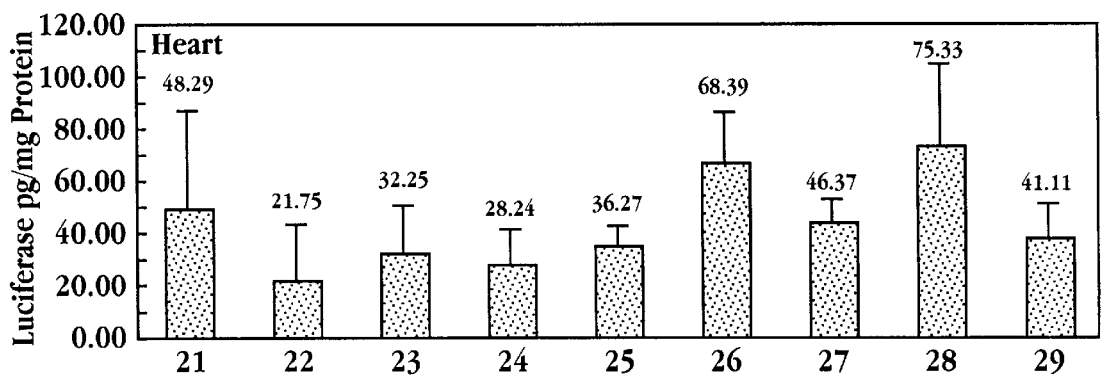
Figure 10D:
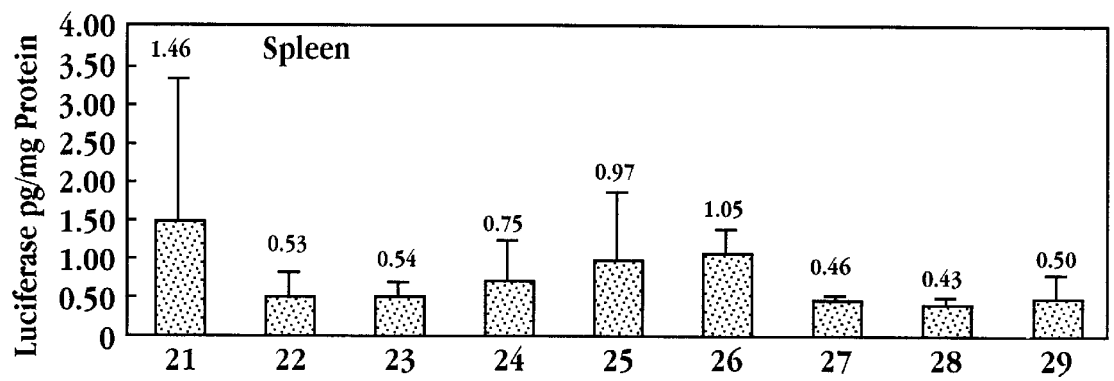
Figure 10E:
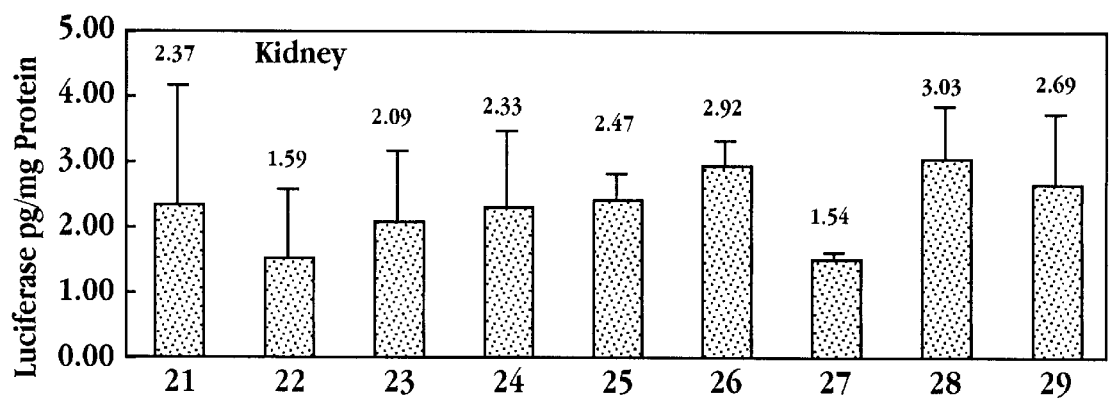

The results of in vivo administration in mice of the plasmid-liposome complexes in Table 4 are shown in FIGS. 10A–10E, where luciferase expression, in pg luciferase/mg protein, is shown in the lung (FIG. 10A), liver (FIG. 10B), heart (FIG. 10C), spleen (FIG. 10D) and kidney (FIG. 10E). The ratio lipid/plasmid ratio for each of the formulations was constant at 14 nmoles lipid/$\mu$g plasmid, falling in the preferred range of 8–18 nmoles liposome lipid/$\mu$g plasmid.

These studies using a variety of polycationic condensing agents, e.g., total histone, histone H1, histone H4, poly-1-glutamine, melittin and polymyxin B, indicate that the highest transfection is achieved where the liposome lipid/plasmid ratio (in nmoles lipid/$\mu$g plasmid) is greater than 10 and less than about 15. More preferably, the ratio is between 12–14 nmoles liposome lipid/$\mu$g plasmid.

As discussed above, the plasmid-liposome complex of the present invention is stable, as evidenced by little change in particle size (see FIG. 5), for at least 30 days at 4° C. The expression stability of the complex was determined by administering plasmid-liposome complexes which were stored at 4° C. to mice. Specifically, the suspension of plasmid-liposome complexes was administered intravenously to mice immediately after preparation of the complex (day 0) and at one week intervals after storage at 4° C. Following the procedure detailed in Example 2, luciferase expression in the lung and liver was determined, and the results are shown in FIGS. 11A–11B.

Figure 11A:
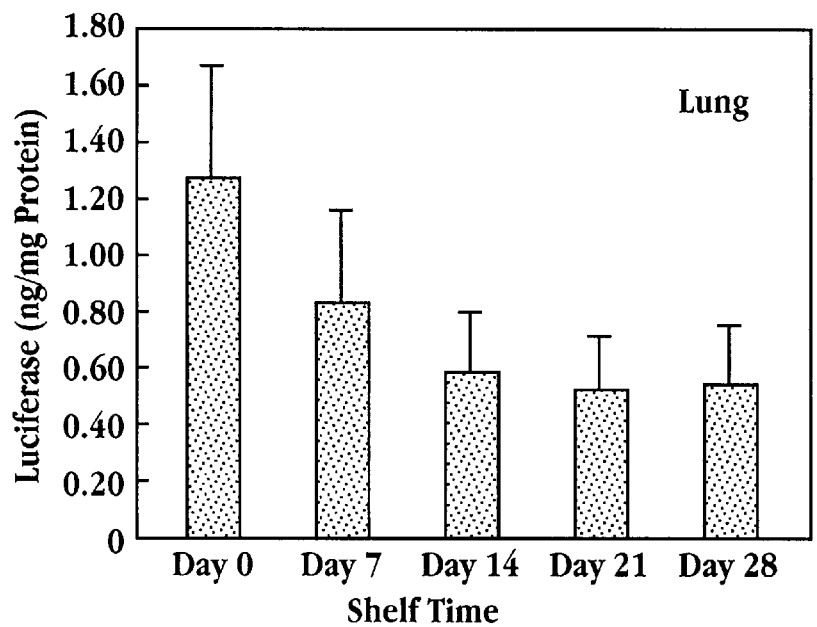
FIGS. 11A–11B show luciferase expression in the lung (FIG. 11A) and the liver (FIG. 11B) as a function of time in days for plasmid-liposome complexes stored at 4° C.
Figure 11B:
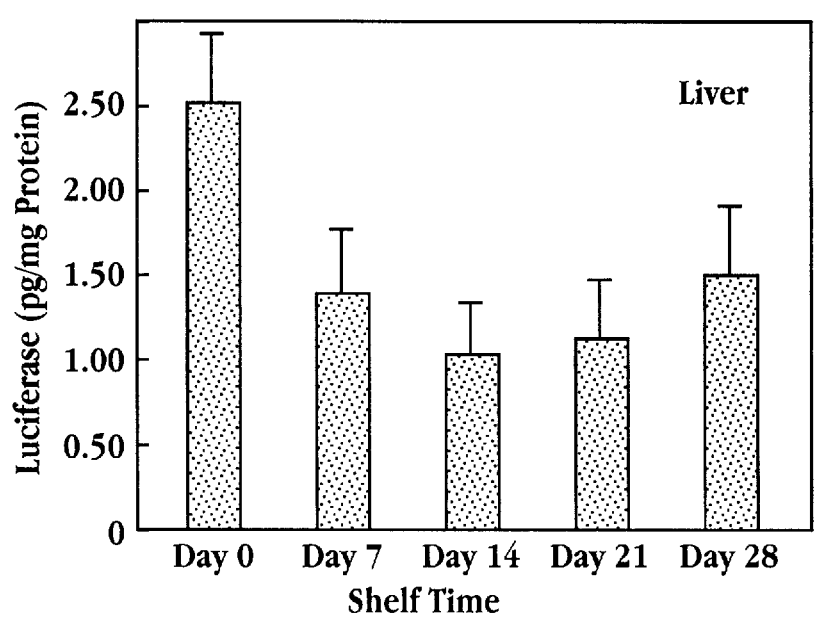

As seen in FIGS. 11A–11B, luciferase expression in the lung (FIG. 11A) and the liver (FIG. 11B) are shown as a function of time in days. At day 0, the luciferase expression in the lung was about 1.3 ng luciferase/mg protein and 2.5 pg luciferase/mg protein in the liver. After one week of storage, the transfection activity had decreased to about 0.8 ng/mg protein in the lung and 1.5 pg/mg protein in the liver. With subsequent storage, the transfection activity remained constant and at day 28, that is after 4 weeks of storage at 4° C., the plasmid-liposome complex retained more than 50% of the expression measured at day 0.

Figure 12:
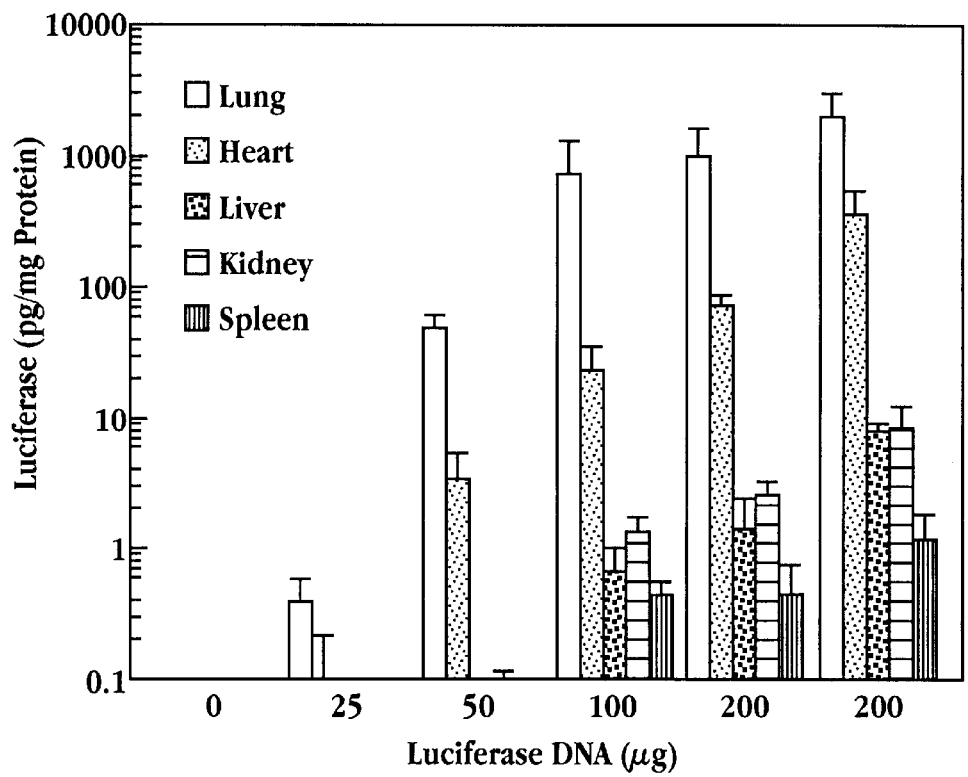
FIG. 12 shows luciferase in various tissues, in pg/mg protein, at 24 hours after intravenous administration in mice of plasmid-liposome complexes, as a function of micrograms of luciferase-carrying plasmid administered.

A dose-response study was performed using plasmid-liposome complexes prepared as described in Example 1. The plasmid-liposome complex was administered intravenously in mice at five dosage levels of plasmid: 25, 50, 200 250 and 200 µg. Twenty-four hours after administration, luciferase expression in the lung, heart, liver, kidney and spleen was measured, and the results are shown in FIG. 12. The luciferase expression measured was proportional to the dose administered, with the highest expression in the lung.

Figure 13:
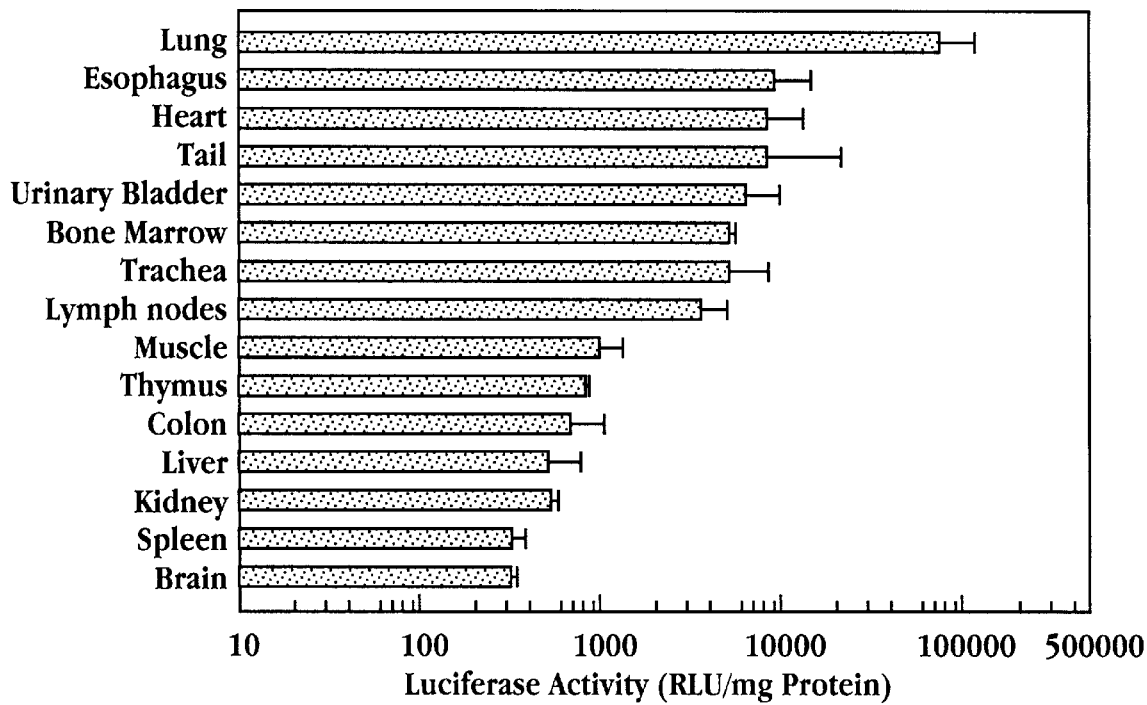
FIG. 13 shows luciferase activity, in RLU/mg protein, in various tissues 24 hours after intravenous administration of plasmid-liposome complexes.

The systemic luciferase expression 24 hours following administration of the plasmid-liposome complex in mice is shown in FIG. 13. The plasmid-liposome complex distributes widely, as evidenced by luciferase expression in the bone marrow, lymph nodes and brain.

From the foregoing, it can be appreciated how various features and objects of the invention are met. Plasmid-liposome complexes prepared in accordance with the method of the invention for a substantially homogeneous population having sizes in the range of 120–180 nm, as evidenced by dynamic light scattering. The complexes are stable for at least 30 days, with no aggregation of complexes, as evidenced by dynamic light scattering. Importantly, the transfection activity of the complexes is also stable, where the complexes retain more than 50% of transfection efficiency after storage for 30 days at 4° C. The plasmid-liposome complexes achieve a transfection efficiency of greater than 25 nm luciferase/mg protein, as evidenced by in vivo administration of a complex containing a plasmid carrying a luciferase reporter gene and post-administration analysis of the liver.

IV. EXAMPLES

The following examples illustrate methods of preparing, characterizing, and using the plasmid-liposome particles of the present invention. The examples are in no way intended to limit the scope of the invention.

V. Materials and Methods

A. Lipids

Dimethyldioctadecylammonium (DDAB) was purchased from Avanti Polar Lipids, Inc. (Birmingham, Ala.). Cholesterol, greater than 99% pure, was obtained from Nu-Chek (Elysian, Minn.).

B. Polycationic Condensing Agents

Total histone, consisting of a mixture of histones, including H1, H2, H3 and H4, histone H1 and histone H4 were obtained from Boehringer Mannheim (Indianapolis, Ind.). Poly-1-glutamine, melittin and polymyxin B sulfate were obtained from Sigma Chemical Co. (St. Louis, Mo.).

C. Methods: Dynamic Light Scattering

Size distribution measurements were obtained by dynamic light scattering (DLS) using a Coulter N4MD instrument, operated according to the manufacturer's instructions. The results were expressed as the mean diameter in nm and standard deviation of a Gaussian distribution of particles by relative volume.

EXAMPLE 1

Preparation of Plasmid-Liposome Complex

A. Preparation of pNSL Plasmid

A pNSL plasmid encoding for luciferase was constructed from two commercially available plasmids, pGFP-N1 plasmid (Clontech, Palo Alto, Calif.) and pGL3-C (Promega Corporation, Madison, Wis.).

The pGL3-C was cut with XbaI and blunt-end ligated using the Klenow fragment of E. coli DNA polymerase. It was then cut with HindIII and the 1689-bp fragment, carrying the luciferase gene, was gel-purified. The pGFP-N1 plasmid was cut with SmaI and HindIII and the 4.7 kb fragment, isolated from an agarose gel, was ligated with the luciferase fragment. JM109 E. coli cells were transformed and 20 colonies were selected; about half of then showed the presence of inserts; 8 clones with inserts were cut with NamHI and XhoI to further confirm the presence of the luciferase gene; 7 of them were positive.

B. Preparation of Cationic Liposomes

Cationic liposomes were prepared according to standard procedures by dissolving 10 µmol DDAB and 10 µmol cholesterol in an organic solvent containing primarily $CHCl_3$. The lipids were dried to a thin film by rotation under reduced pressure. The lipid film was hydrated by addition of distilled water to form a suspension of liposomes at a concentration of 20 µmole/ml. The liposomes were sized by sonication or by sequential extrusion through Nucleopore polycarbonate membranes with pore sizes of 0.4 µm, 0.2 µm, 0.1 µm and 0.05 µm to obtain liposomes of 80–120 nm in size (Nucleopore, Pleasanton, Calif.).

C. Preparation of Condensed Plasmid

The DNA plasmid pNSL encoding for luciferase, prepared as described above, was condensed according to the following procedure. 400 µl of the plasmid (1 mg/ml in distilled water) was diluted with 310 µl distilled water and then mixed with 90 µl of 50% glucose. 100 µl of a polycationic condensing agent (total histone, histone H1, histone H4, poly-1-glutamine, melittin or polymyxin B) from a stock solution of 1 mg/ml in distilled water was added to the plasmid solution slowly with stirring. The mixture was stirred for 10 minutes.

D. Preparation of Complex

Plasmid-liposome complexes having a liposome lipid/plasmid ratio of 14 nmole lipid/µg plasmid was prepared by diluting 280 µl of the liposome suspending with 350 µl of distilled water and then adding 70 µl of 50% glucose. The suspension of condensed plasmids was slowly added to the diluted cationic liposome suspension with continuous stirring for 10 minutes.

EXAMPLE 2

In vivo Transfection Procedure

In vivo transfection with the plasmid-liposome complexes was conducted with BALB/c mice obtained from Simonsen (Gilroy, Calif.). Each plasmid-liposome complex formulation was injected via tail vein into 3 mice. The mice were sacrificed 24 hours after injection and tissues (lung, liver, spleen, kidney, heart) were collected following perfusion with heparinized PBS (4° C.) under anesthesia.

At a temperature of between 0°–4° C., 0.75 ml cell lysis reagent (Promega, Madison, Wis.) was added to each tissue, and the tissue was homogenized for 1 minute at 20,000 rpm. The supernatant was removed to a microcentrifuge tube and spun at 10,000 g for 5 minutes. The supernatant was collected for luciferase and protein assays. 20 $\mu$l of each sample was measured immediately by a luminometer (100 $\mu$l of luciferin and ATP containing assay buffer, 10 second measurement). The relative light unit was normalized by the amount of protein in the extracts.

Although the invention has been described with respect to particular embodiments, it will be apparent to those skilled in the art that various changes and modifications can be made without departing from the invention.

It is claimed:

1. An improvement in a method of preparing plasmid-liposome complexes by condensing plasmid molecules and mixing the condensed plasmids with a suspension of cationic liposomes to form plasmid-liposome complexes for use in transfecting a host cell, said improvement comprising the steps of selecting as a condensing agent for condensing the plasmid molecules, a polycation selected from the group consisting of histones, poly-1-glutamine, melittin and polymyxin B, selecting as a medium for suspending said condensed plasmid molecules, a low-ionic strength aqueous medium, and selecting a ratio of liposome lipid to plasmid of greater than 10 nmole liposome lipid/$\mu$g plasmid and less than 15 nmole liposome lipid/$\mu$g plasmid, where the plasmid-liposome complexes produced by the improvement have:
   (i) sizes in the range of 120–180 nm and
   (ii) a transfection stability of at least 30 days, as evidenced by a stable in vivo transfection efficiency of the complex after storage for 30 days at 4° C.

2. The method of claim 1, wherein said condensing agent is selected from the group consisting of total histone, histone 1 and histone 4.

3. The method of claim 2, wherein said condensing agent is total histone.

4. The method of claim 1, wherein said liposome lipid to plasmid ratio is between 12–14 nmole liposome lipid/$\mu$g plasmid.

5. The method of claim 1, wherein said low-ionic strength aqueous medium is prepared from a non-ionic osmotic solute.

6. The method of claim 5, wherein said solute is selected from the group consisting of glucose, sucrose and dextran.

7. The method of claim 1, wherein the cationic liposomes are prepared from cholesterol and DDAB.

8. The method of claim 1, wherein said cationic liposomes have a surface coating of polyethylene glycol by including a vesicle-forming lipid derivatized with polyethylene glycol.

* * * * *